United States Patent [19]
Lin et al.

[11] Patent Number: 4,891,442
[45] Date of Patent: Jan. 2, 1990

[54] PROCESS FOR SYNTHESIS OF β-PHENYLALANINE

[75] Inventors: Jiang-Jen Lin, Round Rock; John F. Knifton, Austin, both of Tex.

[73] Assignee: Texaco Inc., White Plains, N.Y.

[21] Appl. No.: 23,326

[22] Filed: Mar. 9, 1987

[51] Int. Cl.$^4$ .............................................. C07C 99/00
[52] U.S. Cl. ................................................... 562/450
[58] Field of Search ......................... 562/443, 450, 408

[56] References Cited

U.S. PATENT DOCUMENTS

| | | | |
|---|---|---|---|
| 3,766,266 | 10/1973 | Wakamatsu et al. | 562/406 |
| 3,867,436 | 2/1975 | Nakamura et al. | 562/443 |
| 3,996,288 | 12/1976 | Yukata et al. | 562/445 |
| 4,264,515 | 4/1981 | Stern et al. | 560/41 |
| 4,497,964 | 2/1985 | Ojima et al. | 562/406 |
| 4,547,590 | 10/1985 | Love et al. | 562/406 |

OTHER PUBLICATIONS

Wakamatsu et al., J. Chem. Soc., Chem., Comm., (1971), p. 1560.

*Primary Examiner*—James H. Reamer
*Attorney, Agent, or Firm*—Jack H. Park; Kenneth R. Priem; Cynthia L. Kendrick

[57] ABSTRACT

N-acetyl-β-phenylalanine is synthesized by reacting phenylacetaldehyde, acetamide and synthesis gas with a catalyst comprising a cobalt-containing compound in conjunction with a cocatalyst that may be either a Group VB or VIB containing ligand, or a rhodium compound optionally bonded to one or more Group VB or VIB donor ligands, at a temperature of at least 50° C. and a pressure of at least 500 psi.

3 Claims, No Drawings

PROCESS FOR SYNTHESIS OF β-PHENYLALANINE

FIELD OF THE INVENTION

This invention relates to the selective synthesis of N-acyl-alpha amino acids from the reaction of an aldehyde with an amide of a carboxylic acid and synthesis gas.

More particularly, this invention involves the synthesis of N-acetyl-β-phenylalanine from acetamide and synthesis gas in high yields in the presence of a cobalt catalyst plus a cocatalyst that may be either a Group VB or VIB containing ligand, or a rhodium species optionally bonded to one or more Group VB or VIB donor ligands using mild temperatures and pressures. The N-acetyl-β-phenylalanine may then be converted to β-phenylalanine—a precursor to asparatame, the artificial sweetener.

BACKGROUND OF THE INVENTION

β-phenylalanine is presently one of two ingredients, along with aspartic acid, that is used in the production of aspartame.

Ajinomoto, in 1974, received British Patent No. 1,377,900, dealing with a process in which phenylacetaldehyde was treated with ammonium, cyanide and carbonate ions at 122°-302° F. (50°-150° C.), and the intermediate was hydrolyzed at about 392° F. (200° C.) to produce phenylalanine. The yield was cited as 92.7%.

As recently as 1974, no established industrial method existed for L-phenylalanine production. Currently, both synthesis and fermentation have been investigated. Some of the chemical synthesis methods which have been reviewed by Kaneko et al. (See "Synthetic Production and Utilization of Amino Acids", Halsted Press, New York, 1974, p. 171-179) include using such starting materials as benzaldehyde, aniline, benzyl chloride, ethyl benzylacetoacetate, phenylacetaldehyde and L-tyrosine via various intermediates. Chemical synthesis of phenylalanine normally produces both the D- and L-phenylalanines, which must be resolved and separated. The D-phenylalanine is then racemized, and recycled for further recovery of the L-phenylalanine.

In 1983, Chimie Saline, a subsidiary of ENI was reported to be planning a plant to produce L-phenylalanine methyl ester directly from benzaldehyde, using technology developed by Assoreni, another ENI subsidiary. The process uses an asymmetric hydrogenating catalyst (see European Chem. News, July 18, 1983, p. 15). Phenylalanine is reportedly produced commercially from tyrosine, another amino acid that is isolated from hydrolyzates of natural proteins (see Chem. Mkt. Rep., May 14, 1984, p. 19).

While most current commercial production of L-phenylalanine is by fermentation (see SRI International Report No. 170, September 1984), other recent reports indicate that cinnamic acid can already be used economically to produce L-phenylalanine (European Chem. News, Oct. 29, 1984, p. 21).

The method most commonly used is fermentation, this employes a glucose substrate and a strain of Brevibacterium lactofermentum at 86° F. (30° C.) and a pH of 7.0. The product is collected from the cell-free broth by absorption on a strongly acidic cation exchange resin at a pH of about 2.0, eluted from the resin with dilute ammonium solution, precipitated and dried before it is esterified to L-phenylalanine methyl ester with an excess of methanol in the presence of a sulfuric acid.

There are a number of disclosures in the literature now dealing with the synthesis of α-amino acids and their derivatives using aldehydes as substrates in combination with amides and carbon monoxide.

U.S. Pat. No. 3,766,266 to H. Wakamatsu and J. Uda discloses a method of producing an N-acyl derivative of an α-amino acid which comprises holding an aldehyde, an amide of a carboxylic acid and carbon monoxide at a temperature of 10° to 300° C. and a pressure of at least 500 atm. in the presence of a carbonylation catalyst until said N-acyl-α-amino acid is formed.

In J. Chem. Soc. Chem. Comm. 1540 (1971), Wakamatsu, et al. disclose a cobalt-catalyzed carbonylation reaction which gives various N-acyl amino-acids from an aldehyde, an amide and carbon monoxide. In this disclosure, where phenylacetyladehyde was used as the starting aldehyde, the corresponding N-acetyl-phenylalanine was obtained in modest yield.

An article by Parnaud, et al., in Journal of Molecular Catalysis, 6 (1979) 341-350, discusses the synthesis potential and the catalytic mechanism for the amidocarbonylation reaction wherein N-acyl-α-amino acids are produced by reacting an aldehyde, CO and an amide in the presence of dicobalt octacarbonyl.

In amidocarbonylation, the aldehyde substrate can be generated in situ from allyl alcohol, alkyl halides, oxiranes, alcohols and olefins followed by the reaction with an amide and carbon monoxide to produce an N-acyl-α-amino acid.

U.S. Pat. No. 3,996,288 to Ajinomoto discloses that when an alcohol or certain of its ester derivatives is held at 50° C. to 200° C. and 10 to 500 atm. in the presence of hydrogen, carbon monoxide, the amide of a carboxylic acid, and a carbonylation catalyst, an aldehyde having one more carbon atom than the alcohol or ester is formed in good yield. If the amide has at least one active hydrogen atom on its amide nitrogen, it further reacts with the aldehyde and carbon monoxide to form an N-acylamino acid.

U.S. Pat. No. 4,264,515 by R. Stern et al. discloses a process for obtaining terminal N-acyl-α-amino acids by a reaction catalyzed by a cobalt carbonylation catalyst wherein the aldehyde is produced in situ from olefins and $CO/H_2$ mixtures. An unsaturated vegetable oil or $C_8-C_{30}$ monoolefinic compound is reacted with an amide, carbon monoxide and hydrogen in the presence of a cobalt catalyst. The process is operated in one step and provides for increased selectivity as compared to a two-step process.

A recent review article, published by I. Ojima et al. in Journal of Organometallic Chemistry, 279 (1985), 203-214, discusses the synthesis of N-acetyl-α-amino acids from (a) the isomerization-amidocarbonylation of allylic alcohols, (b) the isomerization-amidocarbonylation of oxiranes and (c) the hydroformylation-amidocarbonylation of trifluoropropene. This study contributes much data regarding regioselectivity for various products.

It would be an advance in the art to be able to use amidocarbonylation technology in the "key step" synthesis of β-phenylalanine. It would appear that this could provide a less expensive route to phenylalanine. An inexpensive chemical building block such as styrene oxide could be rearranged to provide the phenylacetaldehyde substrate. A process which provided the phenylalanine precursor in good yield using mild reaction conditions would be especially desirable.

In the instant invention modified amidocarbonylation technology is used in the "key step" synthesis of β-phenylalanine. N-acetylphenylalanine was prepared in ca. 82 mole % yield from the reaction of phenylacetaldehyde, acetamide and CO, by use of a dicobalt octacarbonyl catalyst.

Key features of the invention and distinctions from other work in the art include the following:

(1) The product selectivity is sensitive to the operating temperature. The results at 80° C. are much better than those at 100°–120° C.

(2) The use of certain classes of cocatalyst has been found to stabilize the active cobalt species, as evidenced by cobalt recovery in product solution.

SUMMARY OF THE INVENTION

This invention concerns a method for synthesizing N-acetyl-α-amino acids from the reaction of an aldehyde with an amide of a carboxylic acid and synthesis gas (carbon monoxide plus hydrogen) in the presence of a cobalt catalyst plus a cocatalyst that may comprise, either one or more Group VB or VIB containing ligands, or a rhodium species optionally bonded to one or more Group VB or VIB donor ligands, at a temperature of at least 50° C. and a pressure of at least 500 psi.

DETAILED DESCRIPTION OF THE INVENTION

In the narrower and more preferred practice of this invention N-acetyl-β-phenylalanine is prepared from a mixture of phenylacetaldehyde, acetamide, carbon monoxide and hydrogen by a process which comprises contacting said mixture with a catalyst system comprising a cobalt-containing compound and a cocatalyst that may either be a Group VB or VIB containing ligand, or a rhodium compound optionally bonded to one or more Group VB or VIB donor ligands, at a temperature of at least 50° C. and a pressure of at least 500 psi.

The reaction for producing N-acetyl-β-phenylalanine from phenylacetaldehyde can be represented by the following equation:

Equation I

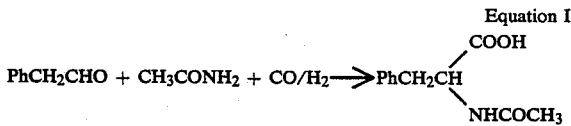

Recovery of the N-acetylphenylalanine from the reaction product can be carried out in any convenient or conventional manner such as by distillation, extraction, filtration, crystallization, etc. In the embodiment of this invention the product was recovered by a simple extraction procedure.

The catalyst system suitable for the practice of this invention comprises a cobalt component plus a cocatalyst. (Comparative data presented INFRA show the advantages of both the cobalt and cocatalyst components). The catalyst combinations of this invention provides the following important advantages over the use of cobalt alone:

(1) It gives higher yields and selectivities of the N-acetylphenylalanine products under milder conditions than can be obtained with a catalyst which utilizes solely a cobalt-containing compound dispersed in a solvent.

(2) It is possible to employ relatively mild operating conditions. In fact, it is found that the results at 80° C. are much better than those at 100°–120° C.

(3) By stabilizing the cobalt-containing compound an additional advantage which is evident is that the cobalt catalyst is easier to recover in the product solution.

The cobalt-containing compound may take many different forms. For instance, the cobalt may be added to the reaction mixture in the form of a variety of inorganic or organic cobalt salts, or cobalt carbonyls. The cobalt may, for example, be added as a cobalt halide, such as cobalt bromide or cobalt chloride, or it may be added as the salt of an aliphatic or aromatic carboxylic acid such as, for example, cobalt formate, cobalt acetate, cobalt butyrate, cobalt naphthenate, and cobalt stearate. The cobalt carbonyl may be tetracobalt dodecacarbonyl or dicobalt octacarbonyl. The preferred cobalt-containing compound is dicobalt octacarbonyl.

In the process of this invention, the Group VB or VIB containing ligands useful as cocatalysts preferably contain one or more tertiary phosphorous, nitrogen or arsenic atoms, or polyvalent sulfur or selenium atoms per molecule.

Suitable tertiary phosphine donor ligands contain one or more trivalent phosphorus atoms per molecule bonded to suitable alkyl, aryl, alkaryl, substituted alkyl, substituted aryl radicals, as well as alkoxy and aryloxy radicals, and mixtures thereof. Suitable alkyl radicals contain 1 to 20 carbons and include methyl, ethyl, n-propyl, iso-propyl, n-butyl, tert-butyl as well as cyclic alkyl radicals such as the cyclohexyl radicals. Suitable aryl radicals may contain 6 to 20 carbon atoms and may include phenyl, o-tolyl, p-tolyl as well as substituted aryl radicals such as p-chlorophenyl and p-methoxyphenyl. Suitable alkoxy radicals may contain 1 to 20 carbon atoms and may include methoxy, ethoxy and butoxy radicals.

Said trivalent phosphorus atoms in the tertiary phosphine donor cocatalyst utilized in the practice of this invention may also be bonded to hydrogen, halogen and nitrogen, as well as to mixtures thereof of the radicals defined above.

Examples of suitable tertiary phosphine donor cocatalysts include tri-n-butylphosphine, triphenylphosphine, tri-n-butylphosphite, tri-c-hexylphosphine, diphenylmethylphosphine, phenyldimethylphosphine, diphenylphosphine, PPh$_2$H, diphenylchlorophosphine, PPh$_2$Cl, hexamethylphosphorus triamide, (Me$_2$N)$_3$P, Di-n-butylchlorophosphine, butyldiphenylphosphine, diethylphosphine, tri-n-hexylphosphine, triethylphosphine, triphenylphosphite, tri-p-tolylphosphine, tri-o-tolylphosphine, tri(m-chlorphenyl)phosphine, tri(p-methoxyphenyl)phosphine and tribenzylphosphine.

Also effective are tertiary phosphine cocatalysts containing two or more trivalent phosphorus atoms per molecule. Here suitable examples include 1,2-bis(diphenylphosphino)ethane, 1,3-bis(diphenylphosphino)propane, Ph$_2$P(CH$_2$)$_3$PPh$_2$, 1,5-bis(diphenylphosphino)pentane and 1,2-bis(diethylphosphino)ethane, as well as 1,2-bis(dimethylphosphino)ethane, 1,1'-bis(diphenylphosphino)ferrocene and 1,1,1-tris(diphenylphosphinomethyl)ethane.

The preferred Group VB donor cocatalyst is 1,2-bis(diphenylphosphino)ethane, Ph$_2$P(CH$_2$)$_2$PPh$_2$, Diphos.

Suitable sulfur-containing cocatalysts for the synthesis of Equation I include soluble/miscible compounds of sulfur-containing one or more sulfur atoms bonded to suitable alkyl, aryl, alkaryl, substituted alkyl, and substituted aryl radicals. The bivalent sulfur atoms may also be bonded to oxygen or to other sulfur atoms.

Examples of suitable sulfur-containing cocatalysts include diphenyl sulfoxide, diphenyl sulfide, phenyl disulfide and ethylsulfide.

A rhodium-containing species is also useful as cocatalyst in the present invention. Any rhodium-containing compounds may be effective to some degree, but preferably they should be capable of forming a rhodium-carbonyl compound under the reaction conditions. This rhodium compound may, for example, be a carbonyl such as hexarhodium hexadecylcarbonyl. Optionally the rhodium compound, or rhodium-carbonyl compound, is complexed with one or more Group VB or VIB donor ligands, such as the phosphine tertiary donor ligands and bivalent sulfur-containing donor ligands described SUPRA.

It is particularly preferred that the rhodium-containing cocatalyst is a rhodium carbonyl triphenylphosphine complex such as hydridocarbonyltris(triphenylphosphine)rhodium(I). This complex may be written as HRh(CO)PPh$_3$)$_3$, where Ph represents a phenyl group.

The feedstock for the practice of this invention is an aldehyde, where the aldehyde function is bonded to an aromatic, aliphatic or arylalkyl moiety. The substrate in the synthesis of N-acetyl-$\beta$-phenylalanine utilizing the chemistry of Equation I is phenylacetaldehyde. This can be supplied relatively inexpensively from styrene, via styrene oxide, from phenylethanol, and from benzyl halides, as illustrated in Equation II.

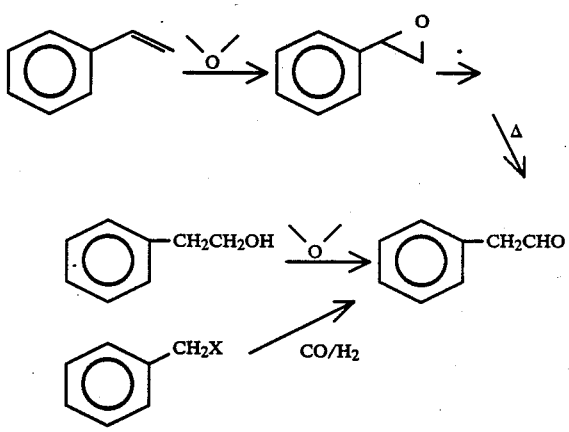

Suitable amide-containing coreactants that are useful in the amidocarbonylation reaction have the general structure:

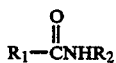

where the R$_1$ and R$_2$ groups may be a combination of aryl, alkyl, arylalkyl and alkylaryl hydrocarbonyl radicals, or hydrogen, including the methyl, ethyl, butyl, n-octyl, phenyl, benzyl and chlorophenyl groupings. Examples of suitable amide coreactants include acetamide, benzamide, formamide, n-methylformamide, lauramide and n-methylbenzamide. The preferred coreactant is acetamide.

As characterized above, this process may be operated as a homogeneous liquid phase mixture. The reaction is preferably operated in an inert solvent. Preferred inert solvents are those which permit at least partial dissolution of the cobalt catalyst precursors, cocatalysts, amide and the aldehyde substrate. These are generally polar solvents, of the ester, ether, ketone, amide, sulfoxide, or aromatic hydrocarbon type, for example.

Methyl and ethyl acetate are examples of suitable solvents. Other polar solvents are ethers, such as p-dioxane, methyl tertiary butyl ether, methyl tertiary amyl ether or tetrahydrofuran, tertiary amides, such as dimethyl formamide, dimethyl sulfoxide and ethylene carbonate.

The preferred solvent is ethyl acetate.

The N-acetylphenylalanine product is soluble in the solvent phase. Separation is normally by solvent extraction. The cobalt catalyst can be recovered from the product solution.

The carbon monoxide employed need not satisfy particular purity requirements although catalyst contaminants should be avoided if the reaction is intended to continue over an extended period. Particularly in continuous operations, but also in batch experiments, the carbon monoxide and hydrogen gas may also be used in conjunction with up to 10% by volume of one or more other gases. These other gases may include one or more inert gases such as argon, nitrogen and the like or they may include gases that may, or may not, undergo reaction under carbon monoxide hydrogenation conditions, such as carbon dioxide, hydrocarbons, such as methane, ethane, propane and the like, ethers, such as dimethyl ether, methyl ethyl ether and diethyl ether, alkanols, such as methanol, and the like.

In all these synthesis in order to achieve a high degree of selectivity the amount of carbon monoxide, phenylacetaldehyde and acetamide present in the reaction mixture should be sufficient to at least satisfy the stoichiometry of the desired formation of N-acetylphenylalanine acid as shown in Equation I above. Excess carbon monoxide over the stoichiometric amount may be present and is desirable.

The quantity of cobalt-containing compounds and cocatalysts to be used in the invention may vary. The process is conducted in the presence of a catalytically effective quantity of the active cobalt-containing compound which gives the desired product in reasonable yield. The reaction proceeds when employing as little as about 0.01 weight percent, and even lesser amounts of the cobalt-containing compound, along with as little as about 0.01 weight percent of the cocatalyst based on the total weight of the reaction mixture. The upper concentration is dictated by a variety of factors including catalyst cost, partial pressures of carbon monoxide and hydrogen, operating temperature, etc. A cobalt-containing compound concentration of from about 0.01 to about 10 weight percent in conjunction with a cocatalyst concentration of from about 0.01 to about 10 percent, based on the total weight of the reaction mixture is generally desirable in the practice of this invention.

The operating conditions may vary over a wide range. The reaction temperature may vary from 25° C. to 300° C. The preferred temperature is from 80° C. to 100° C. It was found that at higher temperatures yields dropped off and there were more side reactions. The pressure may range from 500 psi to 3000 psi or more. It was found that the best yields of N-acetyl-β-phenylalanine were obtained at pressures and temperatures in the range of 800–2500 psi and 80°–100° C., respectively.

The amidocarbonylation reaction of this invention is best conducted in a carbon monoxide-rich atmosphere, although some hydrogen gas should also be present in order to achieve maximum cobalt catalyst activity. The hydrogen to carbon monoxide molar ratio in the reactor may be varied, for example, within the range from 20:1 to 1:20, but preferably it should be rich in carbon monoxide and the $H_2$:CO ratio should be in the range 5:1 to 1:5.

The desired product of the synthesis using phenylacetaldehyde is N-acetyl-β-phenylalanine. Also formed are significant amounts of other amide, ester and aldehyde products. Each of these products, including by-products can be recovered from the reaction mixture by conventional means, e.g., solvent extraction, crystallization or filtration.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired amino acid product, and said material may be recovered by methods known to the art, such as solvent extraction, filtration, recrystallization distillation, membranes and the like. A fraction rich in the catalyst components may then be recycled to the reaction zone, if desired, and additional products generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analysis, or a combination of these techniques. Analysis have for the most part, been by molar weight; all temperatures are in degrees centigrade and all pressures in pounds per square inch (psi).

The yield (mole %) of N-acetylphenylalanine in this synthesis using phenylacetaldehyde is estimated basis equation I using the formula:

$$\frac{\text{Moles of N—acetylphenylalanine obtained}}{\text{Moles of phenylacetaldehyde charged}} \times 100\%$$

To illustrate the process of the invention, the following examples are given. Examples I–XVI demonstrate the method of using phenylacetaldehyde in the process of this invention. It is to be understood, however, that the examples are given in the way of illustration and are not to be regarded as limiting the invention in any way.

EXAMPLE I

A glass-lined autoclave was charged with dicobalt octacarbonyl (0.68 g, 2.0 mmoles), 1,2-bis(diphenylphosphino)ethane (0.20 g), phenylacetaldehyde (6.0 g), acetamide (3.0 g) and ethyl acetate (15.0 g). The reactor was purged with CO/$H_2$ mixture (1:1 molar ratio) to 1000 psi and with pure CO to a final pressure of 2000 psi (resulted ca. 3:1 ratio of CO to $H_2$). The system was heated to 80° C. and held for four hours. During the process, the pressure went up to 2175 psi and then dropped to 2100 psi which indicated the gas consumption. After the reactor was cooled to room temperature, a deep-brown homogeneous solution (ca. 25.9 g) was recovered. A portion of product solution was subjected to a high-vacuum to remove solvent and then analyzed. N-acetylphenylalanine was obtained at ca. 72 mole % yield based on phenylacetaldehyde charged. The cobalt analysis showed 9950 ppm cobalt in product solution; estimated cobalt recovery in solution was >98%.

EXAMPLE II

The experimental procedure of Example I was repeated, except using $Co_2(CO)_8$ (0.68 g), diphenyl sulfoxide (0.20 g), phenylacetaldehyde (6.0 g), acetamide (3.0 g) and ethyl acetate (15 g). The initial pressure was 1000 psi of CO/$H_2$ =1:1, plus 1000 psi of pure CO, resulting in 2000 psi total pressure of CO/$H_2$. The operating conditions were 80° C. and 4 hours. The resulting product solution was homogeneous dark brown solution. The analysis of H—nmr indicated the desired product -βphenylacetaldehyde was the major product with small amount of impurity. The cobalt in the product solution was ca. 7940 ppm; estimated cobalt recovery in solution was 80%.

COMPARATIVE EXAMPLE III

The above experiment was repeated, except using $Co_2(CO)_8$ (0.68 g), phenylacetaldehyde (6.0 g), acetamide (3.0 g) and ethyl acetate (15 g). The reaction conditions were CO/$H_2$ at 3:1 ratio, 2300 psi, 80° C. and 4 hours. The resulting product solution was analyzed indicating ca. 82% yield based on phenylacetaldehyde charged. However, the cobalt analysis showed only 4170 ppm in product solution (ca. 46% cobalt recovery in solution, based on the theoretical 9100 ppm).

EXAMPLE IV

The experimental procedures of Example I were repeated except using $Co_2(CO)_8$ (0.34 g), phenylacetaldehyde (6.0 g), acetamide (3.0 g) and toluene (15 g). The reaction conditions were 1000 psi of CO/$H_2$=1:1, and 2 hours. The resulting reaction mixture was analyzed by H—nmr, indicating only a trace amount of desire product, I plus II and other unidentified products.

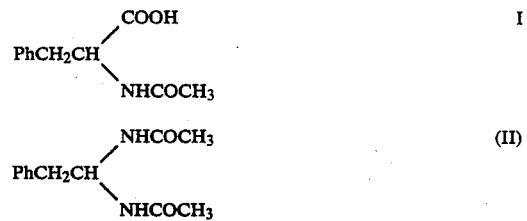

EXAMPLE V

The experimental procedures of Example IV were repeated, except using $Co_2(CO)_8$ (0.68 g), phenylacetaldehyde (6.0 g), acetamide (3.0 g), methanol (3.0 g) and ethyl acetate (15 g). The operating conditions were 2000 psi of CO/$H_2$ mixture at 3:1 ratio, 80° C. and 4 hours. The resulting product solution was analyzed by H—nmr, indicating the presence of an ester of phenylalanine (III) at ca. 58% yield.

EXAMPLE VI

The same experimental procedures were employed, except using 120° C. reaction temperature. The mixture of $Co_2(CO)_8$ (0.34 g), phenylacetaldehyde (6.0 g), acetamide (3.0 g) and ethyl acetate (15.0 g) was subjected to reaction conditions of 2000 psi of $CO/H_2$ at 3:1 molar ratio, 120° C. and 2 hours. The resulting product solution was analyzed by H—nmr and showed ca. 55 mole % N-acetyl-$\beta$-phenylalanine based on phenylacetaldehyde charged.

EXAMPLE VII

The same experimental procedures were employed, except using $HRh(CO)(PPh_3)_3$ (0.046 g), $Co_2(CO)_8$ (0.34 g), phenylacetaldehyde (6.0 g), acetamide (3.0 g) and ethyl acetate (15 g). The pressure of $CO/H_2$ mixture in the ratio of 1:1 at 2000 psi and 100° C. operating temperature were used for three hours reaction time. The recovered liquid product was analyzed to contain N-acetylphenylalanine at 35% product selectivity.

EXAMPLE VIII

The same experimental procedures were employed, except using $HRh(CO)(PPh_3)_3$ (0.046 g, 0.05 mmole), $Co_2(CO)_8$ (0.68 g, 2.0 mmole), phenylacetaldehyde (9.0 g), acetamide (9.0 g) and ethyl acetate (20 g). The operating conditions were $CO/H_2$ (1:1 ratio), 800 psi, 100° C. and 5 hours. The product solution contained N-acetylphenylalanine (I) and compound II in a 1:3 molar ratio.

EXAMPLES IX to IXV

The amidocarbonylation of phenylacetaldehyde was investigated in continuous unit equipment using a stirred tank, 300 ml capacity reactor. Summary data, for a series of eight runs over a spectrum of conditions, are given in Table 1. Product solutions were generally analyzed by nmr to determine the concentration of desired amidoacid. Feeding the liquid reactants plus catalyst in two streams (phenylacetaldehyde, ethyl acetate, $Co_2(CO)_8$, 1,2-bis(diphenylphosphino)ethane (DIPHOS) in stream 1, acetamide, ethyl acetate, methanol in stream 2, feed rates, 20 cc/hr) and operating the carbonylation step at 80° C., 2000 psi with 1/1, $CO/H_2$ syngas (20 1/hr), the crude liquid product under equilibrium conditions, after solvent stripping, comprised 25% of the desired product, N-acetyl-$\beta$-phenylalanine (see Example IX). This and similar samples also showed the presence of unreacted acetamide and some diamide formation.

A subsequent run (Example X) with less acetamide (2, 10 cc/hr) produced crude product that, after stripping, comprised 53% of the desired product. The liquid mass balance, however, was poor because of solvent losses attributable to the high gas flows employed in these runs and the lack of adequate liquid traps.

A third experiment at lower gas (10 1/hr) and liquid (1, 10 cc/hr; 2, 5 cc/hr) feed rates provided liquid effluent that, after stripping, contained 37% of the desired product. In this case the material balance for the liquid in-out was better than 95% (Example XI).

Subsequent runs at higher reaction temperatures (100°, 120° C.), using additional traps in order to maintain good liquid material balances, failed to lead to a substantial improvement in the quantity of desired product, although a positive material balance was achieved in experiments such as Examples XII, XIV and XVI.

TABLE I

PHENYLACETALDEHYDE AMIDOCARBONYLATION

| Example | Oper. Temp. (°C.) | Feed Rate (cc/hr) Stream 1[a] | Feed Rate (cc/hr) Stream 2[b] | Gas Rate (1/hr) | Hold Time (hr) | N—acetyl-$\beta$-phenylalanine Product[d] Conc. (nmr)[c] (%) | Conc. (wt) (%) | Material Feed in (g) | Balance[d] Recovered g |
|---|---|---|---|---|---|---|---|---|---|
| IX | 80 | 20 | 20 | 20 | 4.5 | 25 | | 152 | 140.5 |
| X | 80 | 20 | 10 | 20 | 6 | 53 | 48 | 85.5 | 73.4 |
| | | | | | | 45 | 45 | 114 | 116.9 |
| XI | 80 | 10 | 5 | 10 | 12 | 37 | 46 | 57 | 62.3 |
| XII | 100 | 20 | 10 | 10 | 6 | 27 | 46 | 71.3 | 129.6 |
| | | | | | | 27 | 46 | 114 | 114.2 |
| XIII | 120 | 20 | 10 | 10 | 6 | None | | | |
| XIV | 100 | 20 | 20 | 10 | 4.5 | 12 | 45 | 152 | 164.2 |
| XV | 100 | 20 | 20 | 5 | 4.5 | Very little | 35 | 133 | 129.7 |
| XVI | 80 | 20 | 10 | 5 | 6 | Very little | 37 | 114 | 118.9 |

[a]Feed stream 1, Catalyst solution : $PhCH_2CHO$, 600 g, 5 mole; $EtOOCCH_3$, 900 g; $Co_2(CO)_8$, 34.2 g, 100 mmole; DIPHOS, 10. g, 25.1 mmole
[b]Feed stream 2, Amide solution : $CH_3CONH_2$, 400 g; $EtOOCCH_3$, 800 g; MeOH, 80 g
[c]Analysis is by $^1H$ nmr, measured by total proton area
[d]Typical product liquid sample

What is claimed is:

1. A process for producing N-acetyl-$\beta$-phenylalanine which comprises reacting phenylacetaldehyde, acetamide and synthesis gas with a catalyst consisting essentially of dicobalt octacarbonyl and a cocatalyst comprising a rhodium carbonyl triphenylphosphine complex, at a temperature of 80° to 100° C. and a pressure of 800 to 2500 psi in the presence of a solvent from the group consisting of methyl acetate, ethyl acetate and p-dioxane.

2. The process of claim 1 wherein the cocatalyst is hydridocarbonyl tris(triphenylphosphine)rhodium(I).

3. The process for producing N-acetyl-$\beta$-phenylalanine which comprises reacting phenylacetaldehyde, acetamide and synthesis gas with a catalyst consisting essentially of dicobalt octacarbonyl plus a cocatalyst selected from the group consisting of 1,2-bis(diphenylphosphino)ethane and diphenylsulfoxide, at a temperature of 80° to 100° C. and a pressure of 800 psi to 2500 psi.

* * * * *